(12) United States Patent
Stoehr

(10) Patent No.: US 7,718,161 B2
(45) Date of Patent: May 18, 2010

(54) METHOD FOR TREATING A MOTONEURON DISORDER

(75) Inventor: Thomas Stoehr, Monheim (DE)

(73) Assignee: UCB Pharma GmbH, Monheim (DE)

( * ) Notice: Subject to any disclaimer, the term of this patent is extended or adjusted under 35 U.S.C. 154(b) by 0 days.

(21) Appl. No.: 12/212,864

(22) Filed: Sep. 18, 2008

(65) Prior Publication Data

US 2009/0018198 A1 Jan. 15, 2009

Related U.S. Application Data

(63) Continuation of application No. 11/145,965, filed on Jun. 7, 2005, now abandoned.

(60) Provisional application No. 60/578,063, filed on Jun. 9, 2004.

(30) Foreign Application Priority Data

Jun. 9, 2004 (EP) .................. 04013636

(51) Int. Cl.
 A61K 51/08 (2006.01)
 A61K 38/00 (2006.01)
(52) U.S. Cl. ..................... 424/1.69; 530/300
(58) Field of Classification Search ........................ None
 See application file for complete search history.

(56) References Cited

U.S. PATENT DOCUMENTS

| | | | |
|---|---|---|---|
| 5,773,475 A | 6/1998 | Kohn | 514/616 |
| 5,885,999 A | 3/1999 | Elliott et al. | 514/258 |
| 6,083,941 A | 7/2000 | Farb | 514/177 |
| 6,126,939 A | 10/2000 | Eisenbach-Schwartz et al. | 424/185.1 |
| 6,277,825 B1 | 8/2001 | Olivera et al. | 514/13 |
| 6,420,429 B1 | 7/2002 | Atlas et al. | 514/625 |
| 2004/0101582 A1 | 5/2004 | Wolicki | 424/760 |
| 2005/0227961 A1 | 10/2005 | Kucharik et al. | 514/211.13 |
| 2005/0261204 A1 | 11/2005 | Stoehr | 514/19 |
| 2005/0277596 A1 | 12/2005 | Stoehr | 514/19 |

FOREIGN PATENT DOCUMENTS

| | | |
|---|---|---|
| DE | 24 13 125 | 9/1975 |
| DE | 118629 | 3/1976 |
| DE | 26 27 069 | 1/1977 |
| DE | 27 35 537 | 2/1979 |
| DE | 31 34 933 | 3/1983 |
| DE | 36 13 388 | 10/1986 |
| DE | 195 33 023 | 4/1996 |
| DE | 197 43 140 | 4/1999 |
| DE | 197 43 142 | 4/1999 |
| DE | 197 44 799 | 4/1999 |
| EP | 0 007 441 | 2/1980 |
| EP | 0 038 758 | 4/1981 |
| EP | 0 046 707 | 3/1982 |
| EP | 0 074 070 | 3/1983 |
| EP | 0 194 464 | 9/1986 |
| EP | 0 226 304 | 6/1987 |
| EP | 0 263 506 | 4/1988 |
| EP | 0 000 741 | 7/1989 |
| EP | 0 490 667 | 6/1992 |
| EP | 0 885 186 | 12/1998 |
| EP | 0 997 147 | 5/2000 |
| EP | 1 077 945 | 2/2001 |
| EP | 1 243 263 | 11/2002 |
| WO | WO 94/13651 | 6/1994 |
| WO | WO 97/38980 | 10/1997 |
| WO | WO 97/38981 | 10/1997 |
| WO | WO 98/09953 | 3/1998 |
| WO | WO 99/23078 | 5/1999 |
| WO | WO 99/52519 | 10/1999 |
| WO | WO 00/00463 | 1/2000 |
| WO | WO 01/96286 | 12/2001 |
| WO | WO 02/15937 | 2/2002 |
| WO | WO 02/42256 | 5/2002 |
| WO | WO 02/074297 | 9/2002 |
| WO | WO 02/074784 | 9/2002 |
| WO | WO 02/088664 | 11/2002 |
| WO | WO 2004/108634 | 12/2004 |

OTHER PUBLICATIONS

Federici, 2006, Muscle and Nerve, 33, 302-323.*
Storkebaum, 2005, Nature Neuroscience, 8, 85-92.*
Kieran, 2004, Neuroscience, 125, 427-439.*
Arnt et al. (1984) Pol. J. Pharmacol. Pharm. 36:221-230.
Bennett et al. (2000) Pain 86:163-175.
Beyreuther et al. (2007) CNS Drug Rev. 13(1):21-42.
Blackburn-Munro et al. (2002) Eur. J. Pharmacol. 445:231-238.
Charrier et al. (2003) Molecular Neurobiol. 28(1):51-63.
Chen & Lipton (2006) J. Neurochem. 97:1611-1626.
Eckel et al. (2002) Dtsch. Med. Wochenschr. 127:78-82.
Erichsen & Blackburn-Munro (2002) Pain 98:151-161.
Jimerson et al. (1976) J. Pharm. Pharmacol. 28:845-847.
Mar. 1985 Advanced Organic Chemistry, New York: Wiley, pp. 16-18.
Porter et al. (1984) Cleveland Clinic Quarterly 51(2):293-305.
Schäfers et al. (2003) Pain 104(3):579-588.
Serra et al. (1980) Pharmacol. Res. Comm. 12(6):619-624.
Wood et al. (2004) J. Neurobiol. 61:55-71.
Yezierski et al. (1998) Pain 75:141-155.

* cited by examiner

*Primary Examiner*—Andrew D Kosar
*Assistant Examiner*—Satyanarayana R Gudibande
(74) *Attorney, Agent, or Firm*—Harness, Dickey & Pierce, P.L.C.

(57) ABSTRACT

The present invention is directed to the use of a class of peptide compounds for treating amyotrophic lateral sclerosis (ALS) and other forms of motoneuron diseases and peripheral neuropathies.

11 Claims, 3 Drawing Sheets

METHOD FOR TREATING A MOTONEURON DISORDER

This application is a continuation of application Ser. No. 11/145,965, filed on Jun. 7, 2005, which claims the benefit of U.S. provisional application Ser. No. 60/578,063, filed on Jun. 9, 2004, and of European patent application No. EP 04 013 636.8 filed on Jun. 9, 2004, the entire disclosure of each of which is incorporated herein by reference.

The present invention is directed to the use of a class of peptide compounds for treating amyotrophic lateral sclerosis (ALS) and other forms of motoneuron diseases and peripheral neuropathies.

Certain peptides are known to exhibit central nervous system (CNS) activity and are useful in the treatment of epilepsy and other CNS disorders. These peptides which are described in the U.S. Pat. No. 5,378,729 have the Formula (Ia):

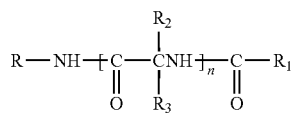

Formula (Ia)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl, lower cycloalkyl lower alkyl, and R is unsubstituted or is substituted with at least one electron withdrawing group or electron donating group;

$R_1$ is hydrogen or lower alkyl, lower alkenyl, lower alkynyl, aryl lower alkyl, aryl, heterocyclic lower alkyl, heterocyclic, lower cycloalkyl, lower cycloalkyl lower alkyl, each unsubstituted or substituted with an electron donating group or an electron withdrawing group; and $R_2$ and $R_3$ are independently hydrogen, lower alkyl, lower alkenyl, lower alkynyl, aryl lower alkyl, aryl, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group or electron donating group;

Z is O, S, $S(O)_a$, $NR_4$, $PR_4$ or a chemical bond;

Y is hydrogen, lower alkyl, aryl, aryl lower alkyl, lower alkenyl, lower alkynyl, halo, heterocyclic, heterocyclic lower alkyl, and Y may be unsubstituted or substituted with an electron donating group or an electron withdrawing group, provided that when Y is halo, Z is a chemical bond, or ZY taken together is $NR_4NR_5R_7$, $NR_4OR_5$, $ONR_4R_7$, $OPR_4R_5$, $PR_4OR_5$, $SNR_4R_7$, $NR_4SR_7$, $SPR_4R_5$ or $PR_4SR_7$, $NR_4PR_5R_6$ or $PR_4NR_5R_7$,

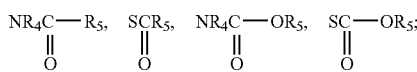

$R_4$, $R_5$ and $R_6$ are independently hydrogen, lower alkyl, aryl, aryl lower alkyl, lower alkenyl, or lower alkynyl, wherein $R_4$, $R_1$ and $R_6$ may be unsubstituted or substituted with an electron withdrawing group or an electron donating group; and $R_7$ is $R_6$ or $COOR_8$ or $COR_8$;

$R_8$ is hydrogen or lower alkyl, or aryl lower alkyl, and the aryl or alkyl group may be unsubstituted or substituted with an electron withdrawing group or an electron donating group; and n is 1-4; and a is 1-3.

U.S. Pat. No. 5,773,475 also discloses additional compounds useful for treating CNS disorders. These compounds are N-benzyl-2-amino-3-methoxy-propionamide having the Formula (IIa):

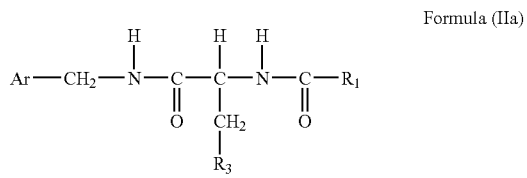

Formula (IIa)

wherein

Ar is aryl which is unsubstituted or substituted with halo; $R_3$ is lower alkoxy; and $R_1$ is methyl.

The patents U.S. Pat. No. 5,378,729 and U.S. Pat. No. 5,773,475 are hereby incorporated by reference. However, neither of these patents describes the use of these compounds as specific neuroprotective agents for the treatment of ALS and other motoneuron diseases as well as peripheral neuropathies.

WO 02/074297 relates to the use of a compound according to Formula (IIa) wherein Ar is phenyl which may be substituted by at least one halo, $R_3$ is lower alkoxy containing 1-3 carbon atoms and $R_1$ is methyl for the preparation of pharmaceutical compositions useful for the treatment of allodynia related to peripheral neuropathic pain.

WO 02/074784 relates to the use of a compound having Formula (Ia) or/and Formula (IIa) showing antinociceptive properties for treating different types and symptoms of acute and chronic pain, especially non neuropathic inflammatory pain, e.g. rheumatoid arthritic pain or/and secondary inflammatory osteo-arthritic pain.

Amyotrophic lateral sclerosis is characterized by degeneration and loss of motoneurons in the anterior horn of the spinal cord and of the brainstem and, to a variable extent, by degeneration of the descending motor pathways within the cortico-spinal tract (Deng et al., 1993; Rothstein et al., 1995). This disorder leads to progressive muscular atrophy, weakness, paralysis and eventually death due to respiratory failure (Andersen et al., 1995). ALS occurs in both familial (FALS) and sporadic (SALS) forms. FALS accounts for 5-10% of cases, with an autosomal dominant pattern of inheritance (Gurney et al., 1994; Rosen et al., 1993). Approximately 20% of the FALS cases have been associated with mutations in SOD1, the gene that encodes for cytosolic Cu, Zn superoxide dismutase (SOD) (Beckman et al., 1993; Rosen et al., 1993). This recent discovery of mutations affecting the SOD gene has given impetus to research on the role of oxidative stress in the pathogenesis of FALS.

In order to establish an animal model for familial ALS, several strains of transgenic mice that carry the human SOD1 gene have been produced. Mice overproducing wild-type human Cu, Zn SOD are clinically normal and in fact show increased resistance to oxidative stress (Yang et al., 1994). Mice producing mutant Cu, Zn SOD rapidly develop a progressive motoneuron disease that strongly resembles ALS (Gurney et al., 1994; Mohajeri et al., 1998). This phenotype occurs in mice expressing the G93A mutation as well as a glycine→arginine mutation (Gurney et al., 1994).

The mechanisms of motoneuron disorders are poorly understood. Current treatments use a variety of pharmacological, surgical, physical and psychological approaches. However, the evidence for many of the treatments is still limited.

The use of compounds of Formula (Ib) or/and Formula (IIb) for treatment of motoneuron disorders has not been reported. Thus, the present invention concerns the use of said compounds of Formulae (Ib) or/and (IIb) for the preparation of a pharmaceutical composition for the prevention, alleviation or/and treatment of motoneuron disorders such as ALS, progressive spinal muscular atrophies or progressive bulbar palsy, or/and peripheral neuropathies such as Guillain-Barré Syndrome or Charcot-Marie-Tooth Syndrome.

Surprisingly, application of compounds (Ib) or/and (IIb), particularly (R)-2-acetamide-N-benzyl-3-methoxypropionamide (SPM 927) exhibited a significant efficacy in prolonging survival and improving motor coordination in mice suffering from motor neuron diseases. Thus, the compounds are useful as medicaments for motoneuron disorders or peripheral neuropathies.

A compound according to the invention has the general Formula (Ib)

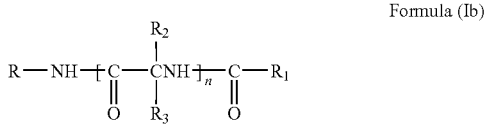

Formula (Ib)

wherein

R is hydrogen, lower alkyl, lower alkenyl, lower alkynyl, aryl, aryl lower alkyl, heterocyclic, heterocyclic lower alkyl, lower alkyl heterocyclic, lower cycloalkyl or lower cycloalkyl lower alkyl, and R is unsubstituted or is substituted with at least one electron withdrawing group, and/or at least one electron donating group;

$R_1$ is hydrogen or lower alkyl, lower alkenyl, lower alkynyl, aryl lower alkyl, aryl, heterocyclic lower alkyl, lower alkyl heterocyclic, heterocyclic, lower cycloalkyl, lower cycloalkyl lower alkyl, each unsubstituted or substituted with at least one electron donating group and/or at least one electron withdrawing group;

and $R_2$ and $R_3$ are independently hydrogen, lower alkyl, lower alkenyl, lower alkynyl, aryl lower alkyl, aryl, halo, heterocyclic, heterocyclic lower alkyl, lower alkyl heterocyclic, lower cycloalkyl, lower cycloalkyl lower alkyl, or Z-Y wherein $R_2$ and $R_3$ may be unsubstituted or substituted with at least one electron withdrawing group and/or at least one electron donating group;

Z is O, S, S(O)$_a$, $NR_4$, $NR'_6$, $PR_4$ or a chemical bond;

Y is hydrogen, lower alkyl, aryl, aryl lower alkyl, lower alkenyl, lower alkynyl, halo, heterocyclic, heterocyclic lower alkyl, lower alkyl heterocyclic and Y may be unsubstituted or substituted with at least one electron donating group and/or at least one electron withdrawing group, provided that when Y is halo, Z is a chemical bond, or ZY taken together is $NR_4NR_5R_7$, $NR_4OR_5$, $ONR_4R_7$, $OPR_4R_5$, $SNR_4R_7$, $NR_4SR_7$, $SPR_4R_5$, $PR_4SR_7$, $NR_4PR_5R_6$, $PR_4NR_5R_7$ or $N^+R_5R_6R_7$,

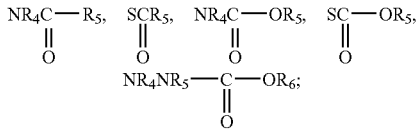

$R'_6$ is hydrogen, lower alkyl, lower alkenyl, or lower alkenyl which may be unsubstituted or substituted with at least one electron withdrawing group or/and at least one electron donating group;

$R_4$, $R_5$; and $R_6$ are independently hydrogen, lower alkyl, aryl, aryl lower alkyl, lower alkenyl, or lower alkynyl, wherein $R_4$, $R_5$ and $R_6$ may independently be unsubstituted or substituted with at least one electron withdrawing group or/and at least one electron donating group;

$R_7$ is $R_6$ or $COOR_8$ or $COR_8$, which $R_7$ may be unsubstituted or substituted with at least one electron withdrawing group or/and at least one electron donating group;

$R_8$ is hydrogen or lower alkyl, or aryl lower alkyl, and the aryl or alkyl group may be unsubstituted or substituted with at least one electron withdrawing group or/and at least one electron donating group; and n is 1-4; and a is 1-3.

Preferably the compound according has the general Formula (IIb)

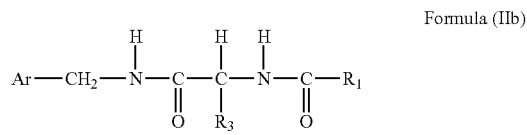

Formula (IIb)

wherein

Ar is aryl, especially phenyl, which is unsubstituted or substituted with at least one halo; $R_3$ is —$CH_2$-Q, wherein Q is lower alkoxy; and $R_1$ is lower alkyl, especially methyl.

The present invention is also directed to a pharmaceutical composition comprising a compound according to Formula (Ib) or/and Formula (IIb) useful for the prevention, alleviation or/and treatment of motoneuron disorders or/and peripheral neuropathies.

The "lower alkyl" groups when used alone or in combination with other groups, are lower alkyl containing from 1 to 6 carbon atoms, especially 1 to 3 carbon atoms, and may be straight chain or branched. These groups include methyl, ethyl, propyl, isopropyl, butyl, isobutyl, tertiary butyl, amyl, hexyl, and the like.

The "lower alkoxy" groups are lower alkoxy containing from 1 to 6 carbon atoms, especially 1 to 3 carbon atoms, and may be straight chain or branched. These groups include methoxy, ethoxy, propoxy, butoxy, isobutoxy, tert-butoxy, pentoxy, hexoxy and the like.

The "aryl lower alkyl" groups include, for example, benzyl, phenylethyl, phenylpropyl, phenylisopropyl, phenylbutyl, diphenylmethyl, 1,1-diphenylethyl, 1,2-diphenylethyl, and the like.

The term "aryl", when used alone or in combination, refers to an aromatic group which contains from 6 up to 18 ring carbon atoms and up to a total of 25 carbon atoms and includes the polynuclear aromatics. These aryl groups may be monocyclic, bicyclic, tricyclic or polyclic and are fused rings. A polynuclear aromatic compound as used herein, is meant to encompass bicyclic and tricyclic fused aromatic ring systems containing from 10-18 ring carbon atoms and up to a total of 25 carbon atoms. The aryl group includes phenyl, and the polynuclear aromatics e.g., naphthyl, anthracenyl, phenanthrenyl, azulenyl and the like. The aryl group also includes groups like ferrocenyl. Aryl groups may be unsubstituted or mono or polysubstituted with electron withdrawing or/and electron donating groups as described below.

"Lower alkenyl" is an alkenyl group containing from 2 to 6 carbon atoms and at least one double bond. These groups may be straight chained or branched and may be in the Z or E form. Such groups include vinyl, propenyl, 1-butenyl, isobutenyl, 2-butenyl, 1-pentenyl, (Z)-2-pentenyl, (E)-2-pentenyl, (Z)-4-methyl-2-pentenyl, (E)-4-methyl-2-pentenyl, pentadienyl, e.g., 1, 3 or 2,4-pentadienyl, and the like.

The term "lower alkynyl" is an alkynyl group containing 2 to 6 carbon atoms and may be straight chained as well as branched. It includes such groups as ethynyl, propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like.

The term "lower cycloalkyl" when used alone or in combination is a cycloalkyl group containing from 3 to 18 ring carbon atoms and up to a total of 25 carbon atoms. The cycloalkyl groups may be monocyclic, bicyclic, tricyclic, or polycyclic and the rings are fused. The cycloalkyl may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl, adamantyl, and the like. Cycloalkyl includes the cis or trans forms. Cycloalkyl groups may be unsubstituted or mono or polysubstituted with electron withdrawing or/and electron donating groups as described below. Furthermore, the substituents may either be in endo or exo positions in the bridged bicyclic systems.

The term "electron-withdrawing and electron donating" refer to the ability of a substituent to withdraw or donate electrons, respectively, relative to that of hydrogen if the hydrogen atom occupied the same position in the molecule. These terms are well understood by one skilled in the art and are discussed in Advanced Organic Chemistry, by J. March, John Wiley and Sons, New York, N.Y., pp. 16-18 (1985) and the discussion therein is incorporated herein by reference. Electron withdrawing groups include halo, including bromo, fluoro, chloro, iodo and the like; nitro, carboxy, lower alkenyl, lower alkynyl, formyl, carboxyamido, aryl, quaternary ammonium, haloalkyl such as trifluoromethyl, aryl lower alkanoyl, carbalkoxy and the like. Electron donating groups include such groups as hydroxy, lower alkoxy, including methoxy, ethoxy and the like; lower alkyl, such as methyl, ethyl, and the like; amino, lower alkylamino, di(loweralkyl) amino, aryloxy such as phenoxy, mercapto, lower alkylthio, lower alkylmercapto, disulfide (lower alkyldithio) and the like. One of ordinary skill in the art will appreciate that some of the aforesaid substituents may be considered to be electron donating or electron withdrawing under different chemical conditions. Moreover, the present invention contemplates any combination of substituents selected from the above-identified groups.

The term "halo" includes fluoro, chloro, bromo, iodo and the like.

The term "acyl" includes lower alkanoyl containing from 1 to 6 carbon atoms and may be straight chains or branched. These groups include, for example, formyl, acetyl, propionyl, butyryl, isobutyryl, tertiary butyryl, pentanoyl and hexanoyl.

As employed herein, a heterocyclic group contains at least one sulfur, nitrogen or oxygen ring atom, but also may include several of said atoms in the ring. The heterocyclic groups contemplated by the present invention include heteroaromatics and saturated and partially saturated heterocyclic compounds. These heterocyclics may be monocyclic, bicyclic, tricyclic or polycyclic and are fused rings. They may preferably contain up to 18 ring atoms and up to a total of 17 ring carbon atoms and a total of up to 25 carbon atoms. The heterocyclics are also intended to include the so-called benzoheterocyclics. Representative heterocyclics include furyl, thienyl, pyrazolyl, pyrrolyl, methylpyrrolyl, imidazolyl, indolyl, thiazolyl, oxazolyl, isothiazolyl, isoxazolyl, piperidyl, pyrrolinyl, piperazinyl, quinolyl, triazolyl, tetrazolyl, isoquinolyl, benzofuryl, benzothienyl, morpholinyl, benzoxazolyl, tetrahydrofuryl, pyranyl, indazolyl, purinyl, indolinyl, pyrazolindinyl, imidazolinyl, imadazolindinyl, pyrrolidinyl, furazanyl, N-methylindolyl, methylfuryl, pyridazinyl, pyrimidinyl, pyrazinyl, pyridyl, epoxy, aziridino, oxetanyl, azetidinyl, the N-oxides of the nitrogen containing heterocycles, such as the N-oxides of pyridyl, pyrazinyl, and pyrimidinyl and the like. Heterocyclic groups may be unsubstituted or mono or polysubstituted with electron withdrawing or/and electron donating groups.

The preferred heterocyclics are thienyl, furyl, pyrrolyl, benzofuryl, benzothienyl, indolyl, methylpyrrolyl, morpholinyl, pyridiyl, pyrazinyl, imidazolyl, pyrimidinyl, or pyridazinyl. The preferred heterocyclic is a 5 or 6-membered heterocyclic compound. The especially preferred heterocyclic is furyl, pyridyl, pyrazinyl, imidazolyl, pyrimidinyl, or pyridazinyl. The most preferred heterocyclics are furyl and pyridyl.

The preferred compounds are those wherein n is 1, but di (n=2), tri (n=3) and tetrapeptides (n=4) are also contemplated to be within the scope of the invention.

The preferred values of R is aryl lower alkyl, especially benzyl especially those wherein the phenyl ring thereof is unsubstituted or substituted with electron donating groups or/and electron withdrawing groups, such as halo (e.g., F).

The preferred $R_1$ is H or lower alkyl. The most preferred $R_1$ group is methyl.

The preferred electron donating substituents or/and electron withdrawing substituents are halo, nitro, alkanoyl, formyl, arylalkanoyl, aryloyl, carboxyl, carbalkoxy, carboxamido, cyano, sulfonyl, sulfoxide, heterocyclic, guanidine, quaternary ammonium, lower alkenyl, lower alkynyl, sulfonium salts, hydroxy, lower alkoxy, lower alkyl, amino, lower alkylamino, di(loweralkyl)amino, amino lower alkyl, mercapto, mercaptoalkyl, alkylthio, and alkyldithio. The term "sulfide" encompasses mercapto, mercapto alkyl and alkylthio, while the term disulfide encompasses alkyldithio. Especially preferred electron donating or/and electron withdrawing groups are halo or lower alkoxy, most preferred are fluoro or methoxy. These preferred substituents may be present on any one of the groups in Formula (Ib) or/and (IIb), e.g. R, $R_1$, $R_2$, $R_3$, $R_4$, $R_5$, $R_6$, $R'_6$, $R_7$, $R_8$ and/or $R_{50}$ as defined herein.

The ZY groups representative of $R_2$ and $R_3$ include hydroxy, alkoxy, such as methoxy, ethoxy, aryloxy, such as phenoxy; thioalkoxy, such as thiomethoxy, thioethoxy; thioaryloxy such as thiophenoxy; amino; alkylamino, such as methylamino, ethylamino; arylamino, such as anilino; lower dialkylamino, such as, dimethylamino; trialkyl ammonium salt, hydrazino; alkylhydrazino and arylhydrazino, such as N-methylhydrazino, N-phenylhydrazino, carbalkoxy hydrazino, aralkoxycarbonyl hydrazino, aryloxycarbonyl hydrazino, hydroxylamino, such as N-hydroxylamino (—NH—OH), lower alkoxy amino [(NHOR$_{18}$) wherein $R_{18}$ is lower alkyl], N-lower alkylhydroxylamino [(NR$_{18}$)OH wherein R$_{18}$ is lower alkyl], N-lower alkyl-O-lower alkylhydroxyamino, i.e., [N(R$_{18}$)OR$_{19}$ wherein R$_{18}$ and R$_{19}$ are independently lower alkyl], and o-hydroxylamino (—O—NH$_2$); alkylamido such as acetamido; trifluoroacetamido; lower alkoxyamino, (e.g., NH(OCH$_3$); and heterocyclicamino, such as pyrazoylamino.

The preferred heterocyclic groups representative of R$_2$ and R$_3$ are monocyclic 5- or 6-membered heterocyclic moieties of the formula:

$$\begin{array}{c} A \\ E \diagup \diagdown J \\ | \quad | - R_{50} \\ G \diagdown \diagup L \\ (CH)_n \end{array}$$

or those corresponding partially or fully saturated form thereof wherein n is 0 or 1; and R$_{50}$ is H or an electron withdrawing group or electron donating group;

A, E, L, J and G are independently CH, or a heteroatom selected from the group consisting of N, O, S;

but when n is 0, G is CH, or a heteroatom selected from the group consisting of NH, O and S with the proviso that at most two of A, E, L, J and G are heteroatoms.

When n is 0, the above heteroaromatic moiety is a five membered ring, while if n is 1, the heterocyclic moiety is a six membered monocyclic heterocyclic moiety. The preferred heterocyclic moieties are those aforementioned heterocyclics which are monocyclic.

If the ring depicted hereinabove contains a nitrogen ring atom, then the N-oxide forms are also contemplated to be within the scope of the invention.

When R$_2$ or R$_3$ is a heterocyclic of the above formula, it may be bonded to the main chain by a ring carbon atom. When n is 0, R$_2$ or R$_3$ may additionally be bonded to the main chain by a nitrogen ring atom.

Other preferred moieties of R$_2$ and R$_3$ are hydrogen, aryl, e.g., phenyl, aryl alkyl, e.g., benzyl and alkyl.

It is to be understood that the preferred groups of R$_2$ and R$_3$ may be unsubstituted or mono or poly substituted with electron donating or/and electron withdrawing groups. It is preferred that R$_2$ and R$_3$ are independently hydrogen, lower alkyl, which is either unsubstituted or substituted with electron withdrawing groups or/and electron donating groups, such as lower alkoxy (e.g., methoxy, ethoxy, and the like), N-hydroxyamino, N-lower alkylhydroxyamino, N-loweralkyl-O-loweralkyl and alkylhydroxyamino.

It is preferred that one of R$_2$ and R$_3$ is hydrogen.

It is preferred that n is one.

It is more preferred that n=1 and one of R$_2$ and R$_3$ is hydrogen. It is especially preferred that in this embodiment, R$_2$ is hydrogen and R$_3$ is lower alkyl or ZY;

Z is O, NR$_4$ or PR$_4$; Y is hydrogen or lower alkyl; ZY is NR$_4$NR$_5$R$_7$, NR$_4$OR$_5$, ONR$_4$R$_7$, $$NR_4C-R_5 \quad \text{or} \quad NR_4C-OR_5.$$
$$\quad \parallel \qquad\qquad\qquad \parallel$$
$$\quad O \qquad\qquad\qquad\quad O$$

In another especially preferred embodiment, n=1, R$_2$ is hydrogen and R$_3$ is lower alkyl which may be substituted or unsubstituted with an electron donating or electron withdrawing group, NR$_4$OR$_5$, or ONR$_4$R$_7$.

In yet another especially preferred embodiment, n=1, R$_2$ is hydrogen and R$_3$ is lower alkyl which is unsubstituted or substituted with hydroxy or loweralkoxy, NR$_4$OR$_5$ or ONR$_4$R$_7$, wherein R$_4$, R$_5$ and R$_7$ are independently hydrogen or lower alkyl, R is aryl lower alkyl, which aryl group may be unsubstituted or substituted with an electron withdrawing group and R$_1$ is lower alkyl. In this embodiment it is most preferred that aryl is phenyl, which is unsubstituted or substituted with halo.

It is preferred that R$_2$ is hydrogen and R$_3$ is hydrogen, an alkyl group which is unsubstituted or substituted by at least an electron donating or electron withdrawing group or ZY. In this preferred embodiment, it is more preferred that R$_3$ is hydrogen, an alkyl group such as methyl, which is unsubstituted or substituted by an electron donating group, or NR$_4$OR$_5$ or ONR$_4$R$_7$, wherein R$_4$, R$_5$ and R$_7$ are independently hydrogen or lower alkyl. It is preferred that the electron donating group is lower alkoxy, and especially methoxy or ethoxy.

It is preferred that R$_2$ and R$_3$ are independently hydrogen, lower alkyl, or ZY;

Z is O, NR$_4$ or PR$_4$;

Y is hydrogen or lower alkyl or

ZY is NR$_4$R$_5$R$_7$, NR$_4$OR$_5$, ONR$_4$R$_7$, $$NR_4C-R_5 \quad \text{or} \quad NR_4C-OR_5.$$
$$\quad \parallel \qquad\qquad\qquad \parallel$$
$$\quad O \qquad\qquad\qquad\quad O$$

It is also preferred that R is aryl lower alkyl. The most preferred aryl for R is phenyl. The most preferred R group is benzyl. In a preferred embodiment, the aryl group may be unsubstituted or substituted with an electron donating or electron withdrawing group. If the aryl ring in R is substituted, it is most preferred that it is substituted with an electron withdrawing group, especially on the aryl ring. The most preferred electron withdrawing group for R is halo, especially fluoro.

The preferred R$_1$ is lower alkyl, especially methyl.

It is more preferred that R is aryl lower alkyl and R$_1$ is lower alkyl.

Further preferred compounds are compounds of Formula (Ib) wherein n is 1; R$_2$ is hydrogen; R$_3$ is hydrogen, a lower alkyl group, especially methyl which is substituted by an electron donating or electron withdrawing group or ZY; R is aryl, aryl lower alkyl, such as benzyl, wherein the aryl group is unsubstituted or substituted with an electron donating or electron withdrawing group and R$_1$ is lower alkyl. In this embodiment, it is more preferred that R$_3$ is hydrogen, a lower alkyl group, especially methyl, which may be substituted by electron donating group, such as lower alkoxy, (e.g., methoxy, ethoxy and the like), NR$_4$OR$_5$ or ONR$_4$R$_7$ wherein these groups are defined hereinabove.

The most preferred compounds utilized are those of the Formula (IIb):

Formula (IIb)

$$Ar-CH_2-\overset{H}{\underset{\parallel}{N}}-\overset{H}{\underset{R_3}{C}}-\overset{H}{\underset{\parallel}{C}}-\overset{H}{N}-\overset{}{\underset{\parallel}{C}}-R_1$$
$$\qquad\qquad\quad O \qquad\qquad O$$

wherein

Ar is aryl, especially phenyl, which is unsubstituted or substituted with at least one electron donating group or electron withdrawing group, especially halo, $R_1$ is lower alkyl, especially containing 1-3 carbon atoms; and $R_3$ is as defined herein, but especially hydrogen, loweralkyl, which is unsubstituted or substituted by at least an electron donating group or electron withdrawing group or ZY. It is even more preferred that $R_3$ is, in this embodiment, hydrogen, an alkyl group which is unsubstituted or substituted by an electron donating group, $NR_4OR_5$ or $ONR_4R_7$. It is most preferred that $R_3$ is $CH_2$-Q, wherein Q is lower alkoxy, especially containing 1-3 carbon atoms; $NR_4OR_5$ or $ONR_4R_7$ wherein $R_4$ is hydrogen or alkyl containing 1-3 carbon atoms, R is hydrogen or alkyl containing 1-3 carbon atoms, and $R_7$ is hydrogen or alkyl containing 1-3 carbon atoms.

The most preferred $R_1$ is $CH_3$. The most preferred $R_3$ is $CH_2$-Q, wherein Q is methoxy.

The most preferred aryl is phenyl. The most preferred halo is fluoro.

The most preferred compounds include:
(R)-2-acetamido-N-benzyl-3-methoxy-propionamide;
O-methyl-N-acetyl-D-serine-m-fluorobenzyl-amide;
O-methyl-N-acetyl-D-serine-p-fluorobenzyl-amide;
N-acetyl-D-phenylglycine benzylamide;
D-1,2-(N,O-dimethylhydroxylamino)-2-acetamide acetic acid benzylamide;
D-1,2-(O-methylhydroxylamino)-2-acetamido acetic acid benzylamide.

It is to be understood that the various combinations and permutations of the Markush groups of $R_1$, $R_2$, $R_3$, R and n described herein are contemplated to be within the scope of the present invention. Moreover, the present invention also encompasses compounds and compositions which contain one or more elements of each of the Markush groupings in $R_1$, $R_2$, $R_3$, n and R and the various combinations thereof. Thus, for example, the present invention contemplates that $R_1$ may be one or more of the substituents listed hereinabove in combination with any and all of the substituents of $R_2$, $R_3$, and R with respect to each value of n.

The compounds utilized in the present invention may contain one or more asymmetric carbons and may exist in racemic and optically active forms. The configuration around each asymmetric carbon can be either the D or L form. It is well known in the art that the configuration around a chiral carbon atoms can also be described as R or S in the Cahn-Prelog-Ingold nomenclature system. All of the various configurations around each asymmetric carbon, including the various enantiomers and diastereomers as well as racemic mixtures and mixtures of enantiomers, diastereomers or both are contemplated by the present invention.

In the principal chain, there exists asymmetry at the carbon atom to which the groups $R_2$ and $R_3$ are attached. When n is 1, the compounds of the present invention is of the formula

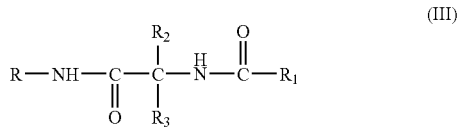

(III)

wherein R, $R_1$, $R_2$, $R_4$, $R_5$, $R_6$, $R'_6$, $R_7$, $R_8$, $R_{50}$, Z and Y are as defined previously.

As used herein, the term configuration shall refer to the configuration around the carbon atom to which $R_2$ and $R_3$ are attached, even though other chiral centers may be present in the molecule. Therefore, when referring to a particular configuration, such as D or L, it is to be understood to mean the D or L stereoisomer at the carbon atom to which $R_2$ and $R_3$ are attached. However, it also includes all possible enantiomers and diastereomers at other chiral centers, if any, present in the compound.

The compounds of the present invention are directed to all the optical isomers, i.e., the compounds of the present invention are either the L-stereoisomer or the D-stereoisomer (at the carbon atom to which $R_2$ and $R_3$ are attached). These stereoisomers may be found in mixtures of the L and D stereoisomer, e.g., racemic mixtures. The D stereoisomer is preferred.

More preferred is a compound of Formula (III) in the R configuration, preferably substantially enantiopure, wherein the substituent R is benzyl which is unsubstituted or substituted with at least one halo group, wherein $R_3$ is $CH_2$-Q, wherein Q is lower alkoxy containing 1-3 carbon atoms and wherein $R_1$ is methyl. Preferably R is unsubstituted benzyl or benzyl substituted with at least one halo group which is a fluoro group.

Depending upon the substituents, the present compounds may form addition salts as well. All of these forms are contemplated to be within the scope of this invention including mixtures of the stereoisomeric forms.

The manufacture of the utilized compounds is described in U.S. Pat. Nos. 5,378,729 and 5,773,475, the contents of both of which are incorporated by reference.

The compounds utilized in the present invention are useful as such as depicted in the Formulae (Ib) or/and (IIb) or can be employed in the form of salts in view of its basic nature by the presence of the free amino group. Thus, the compounds of Formulae (Ib) or/and (IIb) form salts with a wide variety of acids, inorganic and organic, including pharmaceutically acceptable acids. The salts with therapeutically acceptable acids are of course useful in the preparation of formulation where enhanced water solubility is most advantageous.

These pharmaceutically acceptable salts have also therapeutic efficacy. These salts include salts of inorganic acids such as hydrochloric, hydroiodic, hydrobromic, phosphoric, metaphosphoric, nitric acid and sulfuric acids as well as salts of organic acids, such as tartaric, acetic, citric, malic, benzoic, perchloric, glycolic, gluconic, succinic, aryl sulfonic, (e.g., p-toluene sulfonic acids, benzenesulfonic), phosphoric, malonic, and the like.

The present invention is further directed to a method for the prevention, alleviation or/and treatment of a disease or condition as described above in a mammal, including a human being, comprising administering at least one compound of Formulae (Ib) or/and (IIb).

It is preferred that the compound utilized in the present invention is used in therapeutically effective amounts.

The physician will determine the dosage of the present therapeutic agents which will be most suitable and it will vary with the form of administration and the particular compound chosen, and furthermore, it will vary with the patient under treatment, the age of the patient, the type of malady being treated. He will generally wish to initiate treatment with small dosages substantially less than the optimum dose of the compound and increase the dosage by small increments until the optimum effect under the circumstances is reached. When the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents.

In a preferred embodiment, the compounds of the present invention are administered in amounts ranging from about 1 mg to about 100 mg per kilogram of body weight per day, more preferred in amounts ranging from about 1 mg to about 10 mg per kilogram of body weight per day. This dosage regimen may be adjusted by the physician to provide the optimum therapeutic response. Patients in need thereof may be treated with doses of the compound of the present invention of at least 50 mg/day, preferably of at least 200 mg/day, more preferably of at least 300 mg/day and most preferably of at least 400 mg/day. Generally, a patient in need thereof may be treated with doses at a maximum of 6 g/day, more preferably a maximum of 1 g/day and most preferably a maximum of 600 mg/day. In some cases, however, higher or lower doses may be needed.

In another preferred embodiment, the daily doses are increased until a predetermined daily dose is reached which is maintained during the further treatment.

In yet another preferred embodiment, several divided doses may be administered daily. For example, three doses per day may be administered, preferably two doses per day. It is more preferred to administer a single dose per day.

In yet another preferred embodiment, an amount of the compounds of the present invention may be administered which results in a plasma concentration of 0.1 to 15 µg/ml (trough) and 5 to 18.5 µg/ml (peak), calculated as an average over a plurality of treated subjects.

The compounds of Formulae (Ib) or/and (IIb) may be administered in a convenient manner, such as by oral, intravenous (where water soluble), intramuscular, intrathecal or subcutaneous routes. Oral or/and i.v. administration is preferred.

The pharmaceutical composition of the present invention may be prepared for the treatment regimen as described above, in particular for the treatment with doses as described above, to effect plasma concentrations as described above, for administration periods or/and administration routes as specified in the embodiments of the present invention as described above.

In another preferred embodiment, the method of the present invention as described above for the treatment of a mammal including a human being in need thereof comprises administering a compound of the present invention in combination with administering a further active agent for the prevention, alleviation or/and treatment of a motoneuron disorder or/and a peripheral neuropathy. The compound of the present invention and the further active agent may be administered together, i.e. in a single dose form, or may be administered separately, i.e. in a separate dose form. Thus, the pharmaceutical composition of the present invention may comprise a compound of the present invention as defined above and may further comprise a further active agent for the prevention, alleviation or/and treatment of a motoneuron disorder or/and a peripheral neuropathy. The pharmaceutical composition may comprise a single dose form or may comprise a separate dose form comprising a first composition comprising a compound of the present invention as defined above and a second composition comprising the further active agent.

The further active agent for the prevention, alleviation or/and treatment of a motoneuron disorder or/and a peripheral neuropathy may be any suitable agent known to a person skilled in the art.

The compounds of the present invention may be used for the preparation of a pharmaceutical composition as described above.

The compounds of Formulae (Ib) or/and (IIb) may be orally administered, for example, with an inert diluent or with an assimilable edible carrier, or it may be enclosed in hard or soft shell gelatin capsules, or it may be compressed into tablets, or it may be incorporated directly into the fool of the diet. For oral therapeutic administration, the active compound of Formulae (Ib) or/and (IIb) may be incorporated with excipients and used in the form of ingestible tablets, buccal tablets, troches, capsules, elixirs, suspensions, syrups, wafers, and the like. Such compositions and preparations should contain at least 1% of active compound of Formulae (Ib) or/and (IIb). The percentage of the compositions and preparations may, of course, be varied and may conveniently be between about 5 to about 80% of the weight of the unit. The amount of active compound of Formulae (Ib) or/and (IIb) in such therapeutically useful compositions is such that a suitable dosage will be obtained. Preferred compositions or preparations according to the present invention contains between about 10 mg and 6 g active compound of Formulae (Ib) or/and (IIb).

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitoneally. Dispersions can also be prepared in glycerol, liquid, polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying the freeze-drying technique plus any additional desired ingredient from previously sterile-filtered solution thereof.

As used herein, "pharmaceutically acceptable carrier" includes any and all solvents, dispersion media, coatings, antibacterial and antifungal agent, isotonic and absorption delaying agents for pharmaceutical active substances as well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form or ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material an the particular therapeutic effect to be achieved, and (b) the limitations inherent in the art of compounding such as active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 10 mg to about 6 g. Expressed in proportions, the active compound is generally present in from about 1 to about 750 mg/ml of carrier. In the case of compositions containing supplementary active ingredients, the dosages are determined by reference to the usual dose and manner of administration of the said ingredients.

As used herein the term "patient" or "subject" refers to a warm blooded animal, and preferably mammals, such as, for example, cats, dogs, horses, cows, pigs, mice, rats and primates, including humans. The preferred patient is a human.

The term "treat" refers to either relieving the pain associated with a disease or condition, to curing or alleviating the patient's disease or condition or to prolonging survival.

The compounds of the present invention are administered to a patient suffering from the aforementioned type of disorder in an effective amount. These amounts are equivalent to the therapeutically effective amounts described hereinabove.

The following example and figures show the properties of SPM 927 in improving the motor coordination in and prolonging the survival of SOD mutant mice.

The used substance was SPM 927 which is the synonym for Harkoseride. The standard chemical nomenclature is (R)-2-acetamide-N-benzyl-3-methoxypropionamide. The international non-proprietary name of SPM 927 is lacosamide.

FIGURE LEGENDS

EXAMPLE

Figure 1:
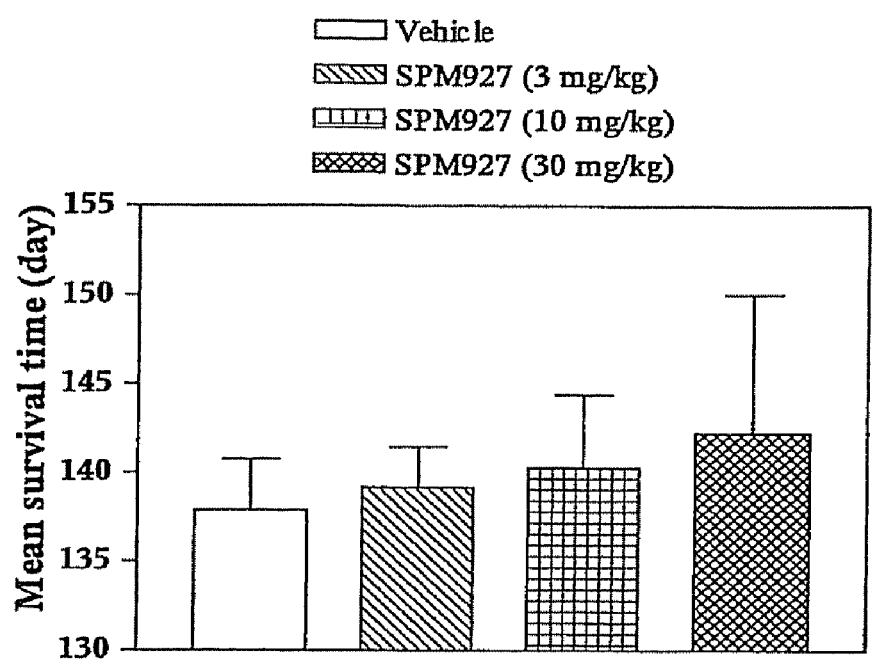
FIG. 1 shows that SPM 927 dose dependently prolongs life-span of SOD mutant mice.

The Effects of SPM 927 in the Sod Mutant Mouse Model of Amyotrophic Lateral Sclerosis (ALS)

This study demonstrates that chronic treatment with SPM 927 attenuates motor symptoms and prolongs survival time in a mouse model of ALS (the SOD mutant mouse). It is shown that SPM 927 treatment attenuates motor symptoms including abnormalities in electrophysiological recordings (EMG) and prolongs survival time after symptom onset in the mouse model.

The present study investigates the effects of SPM 927 to protect or to reduce impairments observed in this ALS model. For this purpose behavioral measurements and EMGs are performed in SOD-G93A mice overexpressing mutant human Cu, Zn SOD.

Materials and Methods

The transgenic mouse strain used for this study is G1H (Gurney et al., 1994). The animals begin to show signs of posterior limb weakness at around 3 months of age and die at 4 months.

40 mice are included in the study and divided into 4 groups of 10 mice.
 a SOD vehicle group
 a SOD treated group (SPM 927 3 mg/kg)
 a SOD treated group (SPM 927 10 mg/kg)
 a SOD treated group (SPM 927 30 mg/kg)

Animals were weighed every day. The general status of the mice was checked daily, especially for the presence of tremor, for skin aspect and for muscle wasting. EMG testing was performed once every week, starting on D70 of age until the death of the animals. The survival rate and the interval from symptom onset until death were recorded.

Motor Coordination Measurements
 Rotarod test: this test evaluates the ability of the animal to stay on a rotating dowel allowing evaluation of motor coordination and proprioceptive sensitivity. The apparatus is a 3 cm diameter automated rod which turns at 12 rounds per minute (Bioseb, Paris, France). The rotarod test measures how long the mouse can maintain itself on the axle without falling. The test is stopped after an arbitrary limit of 120 s. Should the animal fall down before 120 s, the performance is recorded and two additional trials are performed. The mean time of 3 trials is calculated. A motor deficit is indicated by a decrease of walking time.
 Grid test: during the test the mice are placed on a grid (length: 37 cm, width: 10.5 cm, mesh size: 1*1 cm) situated above a plane support. The number of times the mice put their paws through the grid is counted and serves as a measure for motor coordination.

Hanging test: this test evaluates the ability of the animal to hang on a wire. The apparatus is a wire stretched horizontally 40 cm above a table. The animal is attached to the wire by its forepaws. The time needed by the animal to catch the string with its hindpaws is recorded (60 s maximum) during three consecutive trials.

Electrophysiological Measurements

Electromyographic recordings were performed using a Neuromatic 2000M electromyography apparatus. During EMG the mice are anesthetized (60 mg kg-1, Imalgène®). The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mouse. The sciatic nerve is stimulated with a single 0.2 ms pulse at supramaximal intensity (12.9 mA). The amplitude (mV) and the latency of the response (ms) are measured. The amplitude is indicative of the number of active motor units, while distal latency reflects motor nerve conduction velocity.

Drug Administration

The animals were treated from day 60 (before the beginning of the clinical signs) until the animal's death. The treatment was administered twice daily intraperitoneally.

Data Analysis

A global analysis of the data was made using one factor or repeated measures analysis of variance (ANOVA). The Fisher test or the Student-Newman-Keuls t test was used to allow multiple comparisons of individual test groups with a control group or between paired groups. Intra-group analysis was performed to evaluate the variation of performance within each group.

Results

Figure 2:
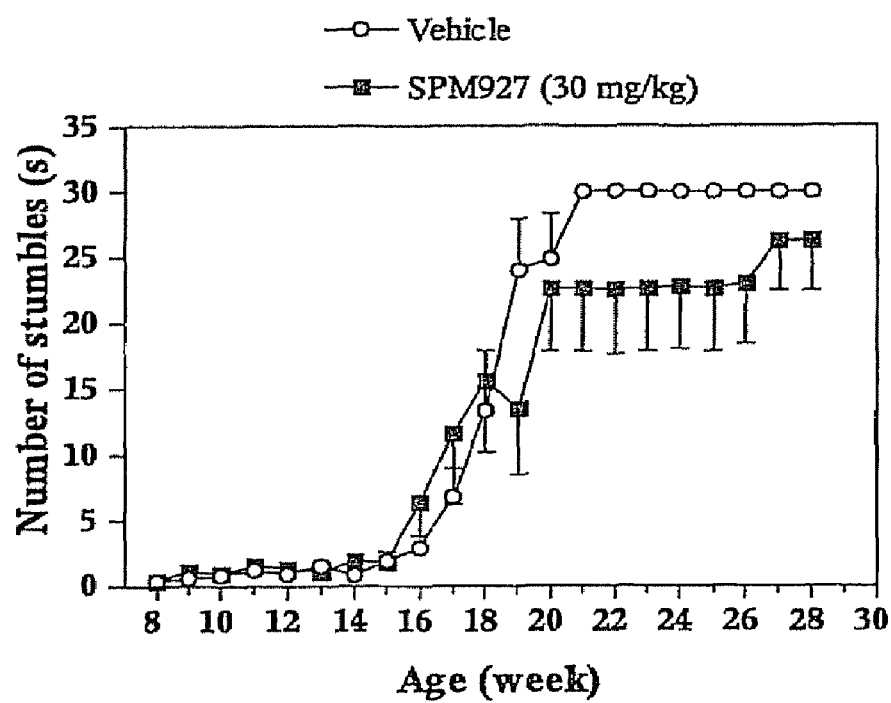
FIG. 2 shows that SPM 927 (30 mg/kg) attenuates motor impairment (grid performance) of SOD mutant mice.
Figure 3:
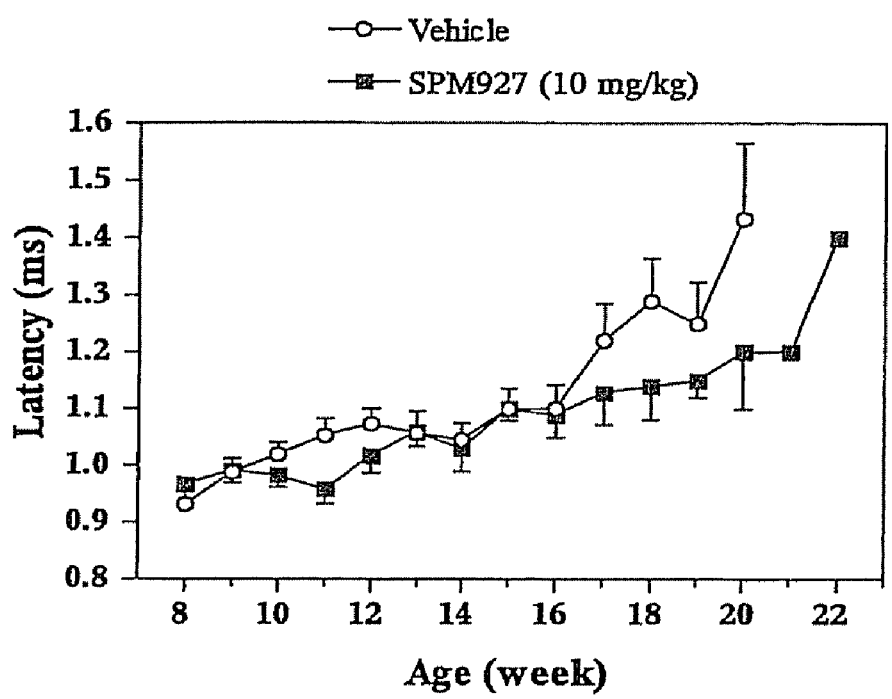
FIG. 3 shows that SPM 927 (10 mg/kg) attenuates motor impairment (latency of compound muscle action potential) of SOD mutant mice.

It was found that SPM 927:
prolongs survival time after onset of symptoms (FIG. 1)
alleviates motor symptoms in the rotarod-, grid-(FIG. 2) and hanging test
attenuates EMG abnormalities (FIG. 3).

CONCLUSION

These results demonstrate that SPM 927 and related compounds are useful for the treatment of amyotrophic lateral sclerosis and for the treatment of other motoneuron diseases including, but not limited to, progressive spinal muscular atrophies and progressive bulbar palsy. In addition, the results show that SPM 927 and related compounds are active for the treatment of peripheral neuropathies including, but not limited to, Guillain-Barré Syndrome or Charcot-Marie Tooth Syndrome.

REFERENCES

ANDERSEN P M, NILSON P, ALA-HURULA V, KERANEN, M L, TARVAINEN I, HALTIA T, NILSSON L, BINZER M, FORSGREN L, MARKLUND S, (1995) *Amyotrophic lateral sclerosis associated with homozygosity for an Asp90A1a mutation in Cu, Zn superoxide dismutase.* Nature Genet. 10: 61-66.

BECKMAN J S, CARSON M, SMITH C D, KOPPENOL W H (1993) *ALS, SOD and peroxynitrite.* Nature 364: 584

BROWN R H, (1995) *Superoxide dismutase in familial amyotrophic sclerosis: models for gain of function.* Curr. Opin. Neurobiol. 5:841-846

DENG H X, HENTATI A, TAINER J A, IQBAL Z, CAYABYAB A, HUNG W Y, GETZOFF E D, HU P, HERZFELDT B, ROOS R P et al. (1993) *Amyotrophic lateral sclerosis and structural defects in Cu, Zn superoxide dismutase.* Science 261: 1047-1051.

GURNEY M E, PU H, CHIU A Y, DAL CANTO M C, POLCHOW C Y, ALEXANDER D D, CALIENDO J, HENTATI A, KWON Y W, DENG H X et al. (1994) *Motor neuron degeneration in mice that express a human Cu, Zn superoxide dismutase mutation.* Science 264:1772-1775.

GURNEY M, CUTTING F B, ZHAI P, DOBLE A, TAYLOR C, ANDRUS P K, HALL E D (1996) *Benefit of vitamin E riluzole, and gabapentin in a transgenic model of familial amyotrophic lateral sclerosis.* Ann. Neurol. 39:147-157.

GURNEY M E (1997) *The use of transgenic mouse model of amyotrophic lateral sclerosis in preclinical drug studies.* J. Neurol. Sci. 152: S67-73

MOHAJERI M H, FIGLEWICZ D A, BOHN M C (1998) *Selective loss of alpha motoneurons innervating the medial gastrocnemius muscle in a model if amyotrophic lateral sclerosis.* Exp. Neurol. 150: 329-336.

ROSEN D R, SIDDIQUE T. PATTERSON D, FIGLEWICZ D A et al. (1993) *Mutations in Cu/Zn superoxide dismutase gene are associated with familial amyotrophic lateral sclerosis.* Nature 362: 59-62.

ROTHSTEIN J D, VAN KAMMEN M, LEVEY A L, MARTIN L J, KUNCL R W (1995) *Selective loss of glial glutamate transporter GLT*-1 *in amyotrophic lateral sclerosis.* Ann. Neurol. 38: 73-84.

YANG G, CHAN P H, CHE J, CARLSON E, CHEN S F, WEINSTEIN P, EPSTEIN C J, KAMII H (1994) *Human copper-zinc superoxide dismutase fransgenic mice are highly resistant to perfusion injury after focal cerebral ischemia.* Stroke 25: 165-170.

The invention claimed is:

1. A method for treating a motoneuron disorder in a subject, comprising administering to the subject a therapeutically effective amount of lacosamide or a pharmaceutically acceptable salt thereof;
   wherein the motoneuron disorder is selected from the group consisting of amyotrophic lateral sclerosis, progressive spinal muscular atrophies, progressive bulbar palsy, Guillain-Barré syndrome and Charcot-Marie-Tooth syndrome.

2. The method of claim 1, wherein lacosamide or salt thereof is administered at a dose of 50 mg/day to 6 g/day.

3. The method of claim 1, wherein lacosamide or salt thereof is administered at a dose of 100 to 600 mg/day.

4. The method of claim 1, wherein lacosamide or salt thereof is administered in a pharmaceutical composition further comprising one or more excipients.

5. The method of claim 4, wherein the composition is administered no more than three times per day.

6. The method of claim 4, wherein the composition and a dose and frequency of administration are selected to result in a plasma concentration of lacosamide of 0.1 to 15 µg/ml (trough) and 5 to 18.5 µg/ml (peak).

7. The method of claim 4, wherein the composition is administered orally or intravenously.

8. The method of claim 1, wherein the subject is a mammal.

9. The method of claim 1, wherein the subject is human.

10. The method of claim 9, wherein the motoneuron disorder is amyotrophic lateral sclerosis.

11. The method of claim 1, wherein lacosamide is administered to the subject.

* * * * *

UNITED STATES PATENT AND TRADEMARK OFFICE
CERTIFICATE OF CORRECTION

PATENT NO.      : 7,718,161 B2                                                Page 1 of 1
APPLICATION NO. : 12/212864
DATED           : May 18, 2010
INVENTOR(S)     : Thomas Stoehr It is certified that error appears in the above-identified patent and that said Letters Patent is hereby corrected as shown below:

Column 1, line 64, "$R_4$, $R_1$ and $R_6$" should be changed to --$R_4$, $R_5$ and $R_6$--
    Column 9, line 66, "R, $R_1$, $R_2$, $R_4$, $R_5$, $R_6$, $R'_6$, $R_7$, $R_8$, $R_{50}$" should be changed to --R, $R_1$, $R_2$, $R_3$, $R_4$, $R_5$, $R_6$, $R'_6$, $R_7$, $R_8$, $R_{50}$--
    Column 12, line 4, "(lib)" should be changed to --(IIb)--.

Signed and Sealed this

Twelfth Day of October, 2010

David J. Kappos
*Director of the United States Patent and Trademark Office*